United States Patent [19]
Mosby

[11] Patent Number: 4,943,991
[45] Date of Patent: * Jul. 24, 1990

[54] CONTOURED IMAGING SYSTEM

[76] Inventor: Richard A. Mosby, 3622 S. Braeswood, Houston, Tex. 77025

[*] Notice: The portion of the term of this patent subsequent to Feb. 27, 2007 has been disclaimed.

[21] Appl. No.: 191,903

[22] Filed: May 9, 1988

Related U.S. Application Data

[63] Continuation-in-part of Ser. No. 155,708, Feb. 16, 1988.

[51] Int. Cl.$^5$ .............................. G03B 42/04
[52] U.S. Cl. ............................ 378/182; 378/147; 378/185; 378/186; 378/203; 378/37; 250/515.1; 206/454; 206/455
[58] Field of Search ............... 378/37, 145, 147–148, 378/154, 159, 185–186, 203, 151, 168–170, 182; 250/363.10, 390.10, 515.1, 505.1, 503.1; 206/454, 455

[56] References Cited

U.S. PATENT DOCUMENTS

| | | | |
|---|---|---|---|
| 3,851,178 | 11/1974 | Borden | 378/168 |
| 3,947,689 | 3/1976 | Wagner | 378/151 |
| 4,122,350 | 10/1978 | Lipthay et al. | 378/37 |
| 4,489,426 | 12/1984 | Grass et al. | 378/147 |
| 4,554,676 | 11/1985 | Maldonado et al. | 378/147 |
| 4,599,738 | 7/1986 | Panetta et al. | 378/37 |
| 4,672,652 | 6/1987 | Huttenrauch et al. | 378/148 |
| 4,739,173 | 4/1988 | Blosser et al. | 250/505.1 |

FOREIGN PATENT DOCUMENTS

| | | | |
|---|---|---|---|
| 2007774 | 9/1971 | Fed. Rep. of Germany | 378/37 |
| 3030332 | 2/1982 | Fed. Rep. of Germany | 378/147 |
| 3437576 | 4/1986 | Fed. Rep. of Germany | 378/37 |
| 3526860 | 1/1987 | Fed. Rep. of Germany | 378/147 |
| 0403400 | 10/1973 | U.S.S.R. | 378/37 |

Primary Examiner—Craig E. Church
Assistant Examiner—John C. Freeman
Attorney, Agent, or Firm—Neal J. Mosely

[57] ABSTRACT

A contoured X-ray imaging system consists of an X-ray source and X-ray film holding cassette for taking X-ray pictures closely adjacent to a body surface without unnecessary exposure of adjacent body parts to X-rays. The X-ray cassette is contoured to the outline of a structure or a body part to evaluate it without the radiation spreading unnecessarily to the adjacent areas. The X-ray cassette is a thin flat box which has an edge wall contoured outline of the subject or an adjacent structure. The X-ray source and intervening shields or the like are each configured to project an X-ray beam which is contoured in the same contour as the film-holding cassette so that the X-rays reach the film in the same contour as avoid unnecessary exposure of adjacent portions of the body to the X-rays.

11 Claims, 3 Drawing Sheets

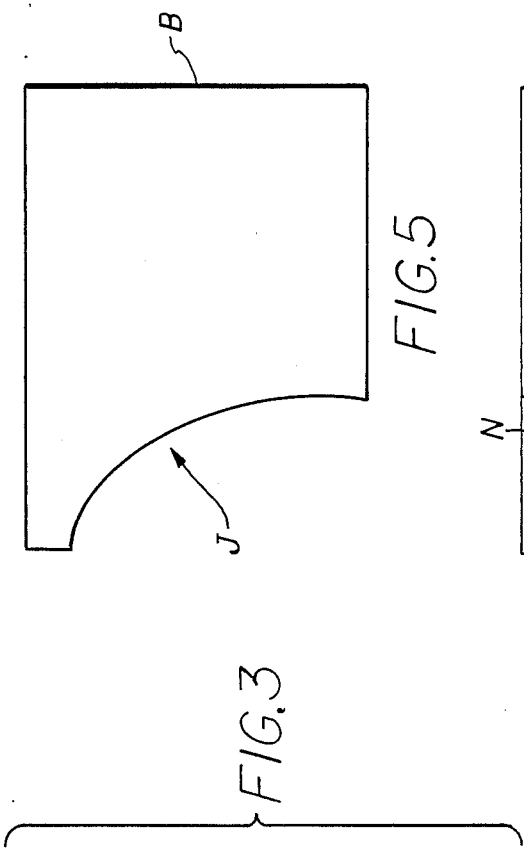
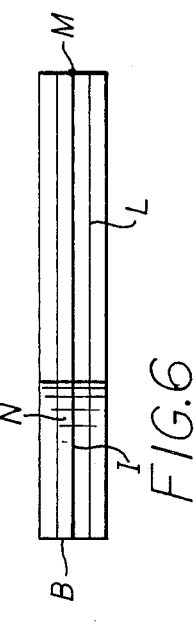
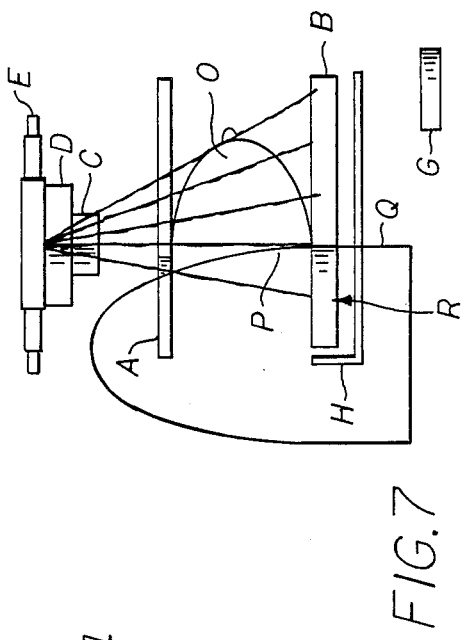
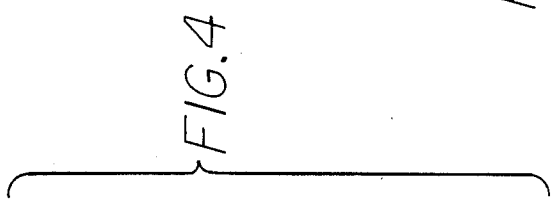
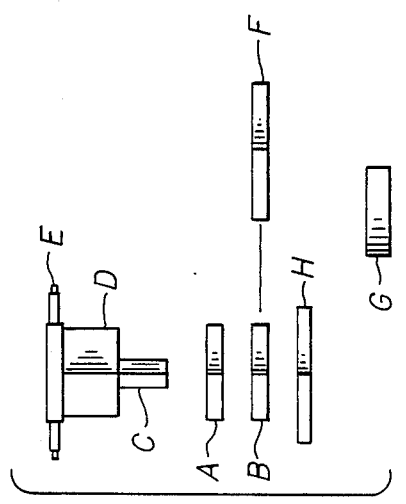
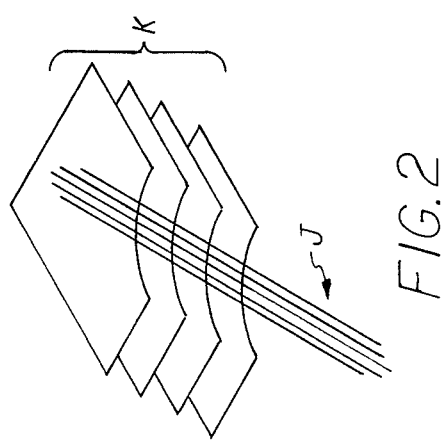

CONTOURED IMAGING SYSTEM

CROSS REFERENCE TO RELATED APPLICATIONS

This application is a continuation-in-part of co-pending application Ser. No. 155,708, filed Feb. 16, 1988.

BACKGROUND OF THE INVENTION

1. FIELD OF THE INVENTION

This invention relates to new and useful improvements in X-ray systems and more particularly to an X-ray system utilizing a contoured X-ray source and a contoured X-ray film cassette having an edge wall portion contoured to fit the surface of an object adjacent or next to the portion of the object to be subjected to X-rays.

2. BRIEF DESCRIPTION OF THE PRIOR ART

The usual imaging systems using X-rays are totally based on the geometric distribution of X-rays and the geometric detection of the X-rays. The usual detection devices for X-rays, e.g. X-ray film cassettes, are constructed in a manner based on the physical properties of the X-ray source. Standard X-ray cassettes are geometric, usually square or rectangular, and do not often conform to the subject or adjacent structure outline, thus limiting subject evaluation.

Cassettes have long been used in energy detecting devices for detection of X-ray and other detectable forms of energy used for examination of the interior of objects. Such cassettes are flat boxes which hold an image fixing medium (X-ray film or the like) in a position adjacent the portion of the object or body being subjected to detection or scanning. Cassettes are usually made of plastic or cardboard. Metal cassettes may be used where the metal does not interfere with the image being detected or fixed.

Standard X-ray cassettes are thin, flat, rectangular (or square) plastic or cardboard boxes which hold the film or other energy detecting medium. The flat edge wall of conventional square or rectangular cassettes often does not conform to the subject or structure outline which limits the subject evaluation or measurement.

In mammography, the standard cassettes used are square or rectangular. This configuration precludes consistent evaluation of deep breast tissue and therefore deep lesions or cancers may go undetected. In industrial uses, the standard cassettes used are likewise square or rectangular which may not conform to the subject or adjacent structure outline.

The contoured imaging system of this invention contours the X-ray source and the X-ray film cassette to more closely conform to the anatomic, physiological and/or structural configuration of the object or adjacent structure being evaluated. The contoured cassette is constructed in a manner based on the physiologic, anatomic and/or structural properties of the subject or adjacent structure being evaluated. This consideration allows more complete evaluation of the subject or adjacent structures. The contoured cassette is so constructed as to conform to subject or adjacent structure outline, enhancing subject evaluation.

In mammography, the standard X-ray energy source is distributed in a geometric pattern to be detected in this geometric pattern by a geometric X-ray film cassette and the film therein. In mammography, standard detection devices are square or rectangular. This configuration precludes consistent evaluation of deep breast tissue and therefore deep lesions or cancers will be undetected. The contoured imaging system of this invention contours the X-ray energy beam or X-ray source to conform to a contoured X-ray film cassette to allow decrease in exposure to radiation of body structures not included in the field of a contoured and contiguous detection device. The primary beam is shielded or absorbed prior to exposure to the X-ray film cassette. The source of X-ray energy is contoured to almost exactly conform to the contoured appearance of the X-ray film cassette. Intervening and supportive structures and materials also are contoured to almost exactly progress the contoured concept throughout the system. Similar contouring of the beam to cassette axis may be used in standard radiography. The contoured cassette is designed, in this instance, to conform to the chest wall inferior to the breast allowing consistent visualization of the deep breast and chest wall.

In industrial uses, standard detection devices do not always conform to the subject or adjacent structure outline. The contoured cassette in such case conforms to the subject or adjacent structure outline and the X-ray source, intervening and supportive structures and materials also contoured to progress the contoured concept throughout the system.

SUMMARY OF THE INVENTION

One object of this invention is to provide an X-ray system that allows the restriction of the source of X-ray energy to almost exactly conform to the outline of a contoured X-ray film cassette.

It is another object of this invention is to provide an X-ray system that allows the restriction of the source of X-ray energy to almost exactly conform to the outline of a contoured X-ray film cassette having an edge wall portion contoured to fit the surface of an object adjacent to the portion of the object to be subjected to X-rays.

Another object of this invention is to decrease exposure to the energy source of adjacent structures by confining the energy beam or source to only the structures being evaluated.

Another object of this invention is to decrease exposure to the energy source of adjacent structures by confining the energy beam or source to only the structures being evaluated and for examination of the interior of objects configured to evaluate portions of the body which are substantially inaccessible.

Another object of this invention is to provide ax X-ray detection system to increase visualization of structures or structures adjacent to them by contouring the X-ray source and the X-ray film cassette so that the X-ray beam conforms to the subject or adjacent structures. In all instances, the configuration of the film cassette determines the configuration of the controlled X-ray energy beam or source.

Another object of this invention, in its medical application, is to contour the X-ray beam to the contour of the edge of an X-ray film cassette to increase the comfort of examination, as in mammography. Presently available cassettes have squared margins and in the use they press against the non-geometric chest wall causing discomfort during the examination. The contoured cassette eliminates this discomfort in that the margins contour with the outline of the thorax allowing close approximation without discomfort. Also, as presently applied, cassettes require that a patient be put in awkward positions to evaluate certain areas of the body, for example, to evaluate the mandible, the patient has to fully extend the neck. The contoured cassette would be made to contour the neck superiorly, not requiring excessive extension to evaluate the mandible.

Another object of the contoured cassette is to develop new and more revealing views of the human body by its configuration and application.

Other objects of the invention will become apparent from time to time throughout the specification and claims as hereinafter related.

These and other objects of the invention are accomplished by an X-ray system where an X-ray energy source is curved, contoured, or otherwise restricted to conform almost exactly, to the outline or contour of a detection device, i.e. X-ray film cassette. All supporting structures associated in the path of the contoured energy source, between the energy source and the detection device and the supporting structures of the detective device, are constructed or designed to complement the general concept. Its benefit is to allow the use of contoured X-ray film cassettes without increased exposure of adjacent structures, not in the source/detection device axis, to the primary beam or source of energy by contouring the source of energy almost exactly to the configuration of the film cassette. The X-ray cassette has an edge wall portion contoured to fit the surface of an object adjacent to the portion of the object to be subjected to X-rays. In use, the cassette is placed adjacent the portion of the object to be X-rayed with the contoured edge wall fitting the surface and permitting X-rays to reach the X-ray film with a minimum of interference.

BRIEF DESCRIPTION OF THE DRAWINGS

FIG. 1 shows a view of the axis from an X-ray tube to a contoured cassette illustrating one preferred embodiment of an X-ray system constituting this invention.

FIG. 2 shows a conceptual demonstration of the contoured X-ray imaging system as an array of stacked intervening structures and contoured energy photos FIG. 3 shows the X-ray energy source/X-ray film cassette axis with the area of the energy beam or source restricted by a collimator and cone device.

FIG. 4 shows the alternative demonstration of FIG. 3 with the contoured shielding material in the collimator and the cone apparatus. The contoured compression plate, the contoured cassette and the contoured cassette holder and/or exposure monitor plate are shown.

FIG. 5 shows a contoured cassette with contoured margin.

FIG. 6 shows a contoured dual cassette with contoured portion shaded.

FIG. 7 shows an application of the contoured X-ray imaging system with the contoured portions shaded.

DESCRIPTION OF THE PREFERRED EMBODIMENT

Figure 12:
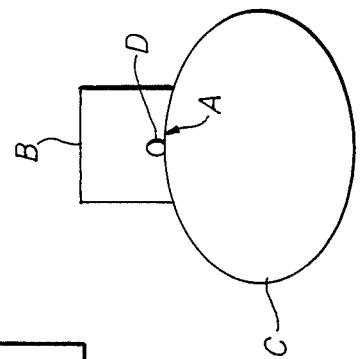
FIG. 12 shows a view of the X-ray cassette consisting of a box for holding an X-ray film having an edge wall portion contoured to fit the stomach and positioned to evaluate an umbilical hernia.

The contoured X-ray imaging system represent an axis formed by a contoured detectable form of energy, i.e., X-rays, contoured intervening structures, and contoured energy detection and support devices, i.e., X-ray cassette. The general purpose is to improve evaluation of structures exposed to the system. The specific purpose of contouring the X-ray energy source is to decrease or eliminate exposure of structures not included in the axis. For example, in mammography, the exposure is limited to the human breast and the contouring of the energy source, X-rays, eliminates or decreases exposure of the human chest wall to X-rays.

FIG. 1 shows a view of the axis from the energy source, E, an X-ray tube in this instance, to the detection device, B, in this instance a contoured cassette, with shaded portions representing the contoured aspects of each structure throughout as in, G, an example of the shading, other lettered structures are the collimator, D, cone device, C, contoured compression plate, A, contoured biopsy plate, F, and contoured cassette holder/exposure monitor plate, H.

FIG. 2 shows a conceptual demonstration of the contoured imaging system as an array of stacked intervening structures and contoured energy photos, K. with limitation of the energy source, X-ray tube, and cut away, that is contoured, aspects of other structures in the energy source/detector axis, J.

FIG. 3 shows the energy source/detector axis with the area of the X-ray energy beam or source restricted by collimator, D, and cone device, C. The edge of the contoured restricting material is shown as jagged oblique line. The cut away, i.e. contoured, portion of subsequent structures in the source/detector axis are seen as A, B, and H. Representing the cut away, i.e. contoured, portions are A, a compression plate, B, a cassette, and H, a cassette holder and/or exposure monitor plate.

FIG. 4 shows the alternative demonstration of FIG. 3 with the contoured shielding material in the collimator, D, and the cone apparatus, C. The contoured compression plate, A, the contoured cassette and the contoured cassette holder and/or exposure monitor plate are shown.

FIG. 5 shows a contoured cassette, B, with contoured margin, J. All structures in the detector aspect of the energy source/detector axis would have similar and complementing outline as in A, B, F, and H, in FIG. 1.

FIG. 6 shows a contoured dual cassette, B, patent applied for, with contoured portion shaded. All internal structures such as X-ray film, L, lead shielding, I, foam support material, N, intensifying screens, grids or any other part of the cassette is contoured, similarly, and as in FIG. 5.

FIG. 7 shows an application of the contoured imaging system with the contoured portions shaded and as, G. Structures as lettered are X-ray tube, E, contoured collimator, D, contoured cone device, C, contoured compression plate, A, contoured cassette, B, with contoured portion, R, and the contoured cassette holder-/exposure monitor device Anatomic structures lettered are human breast, O, with axillary slip, P, and chest wall, Q. The contoured X-ray beam or source is indicated by radiating jagged lines.

Figure 8:
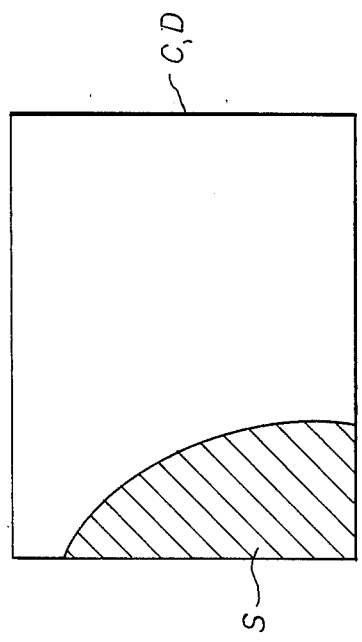
FIG. 8 shows the collimator and cone device from above with shielding material.

FIG. 8 shows the collimator, D, and cone device, C, from above with shielding material, S.

The various sections of the X-ray energy source/detector axis are specifically and complimentary contoured. FIG. 7 shows hoe the detectable energy source or X-rays are contoured by shielding material, such as contoured lead sheet, in the collimator, D, and cone device, C, by placing the shielding material within this structures as in FIG. 8, S. FIG. 7 shows how the remaining structures in the axis are contoured in a complimentary manner, as is the energy source. The compression plate, A, is contoured, the cassette, B, is contoured, and the cassette holder/exposure monitor plate, H, is contoured. This allows the energy source to almost match the configuration of the detection device and supporting or additional structures in the axis, FIG. 5 and 6 indicates that all internal parts of a contoured cassette, film, grids, shielding materials, support material, and intensifying screens are similarly and, almost exactly, contoured to the configuration of the contoured cassette outline. Any device used with the contoured imaging system is similarly contoured as, F, FIG. 1, a contoured biopsy plate.

The cassette is constructed of cardboard, plastic, metal and/or other durable material that has properties which allow the transfer of energy to the detection material or device for detection. The prime feature is that it contour to the surface or interface of the structure or adjacent structure which is to be evaluated. The purpose of this contouring is to enhance and increase the amount of information derived from X-ray examination. The cassette is constructed so that one or several edges are arced in a manner that contours to an adjacent structure or a structure to be evaluated. As an example, in FIGS. 7 and 8, the cassette is contoured to conform to the chest wall structure to evaluate the human breast. The breast, D, and more deep breast tissue and axillary slip are completely submitted for detection. Standard cassettes are so geometric as to preclude this detection. An X-ray beam is presented perpendicularly with respect to the cassette, as is standard, however, the contouring allows more complete evaluation of these structures.

In the various views an X-ray cassette is shown for examination of the interior of objects which consists of a box for holding an image fixing medium having an edge wall portion contoured to fit the surface of an object adjacent to the portion of the object to be subjected to detectable energy. The cassette is constructed of cardboard, plastic, metal and/or other durable materials having properties which permit the transfer of energy to the detection material (film) or device (sonic, magnetic resonance imaging (MRI), etc.) for detection. The cassette has one or more edge walls arced in a manner that allows it to fit or contour to an adjacent structure or a structure to be evaluated. This contouring enhances and increases the amount of information derived from the X-ray examination.

Figure 10:
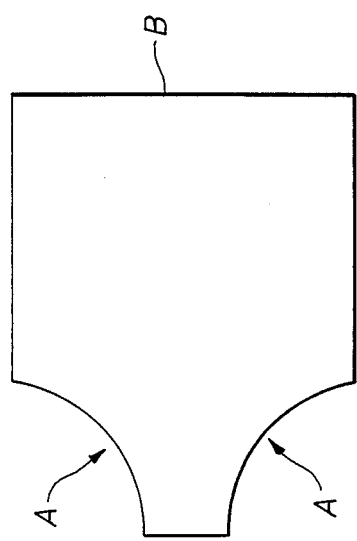
FIG. 10 shows a view of the X-ray cassette consisting of a box for holding an image fixing medium having an edge wall portion contoured for still another application.
Figure 11:
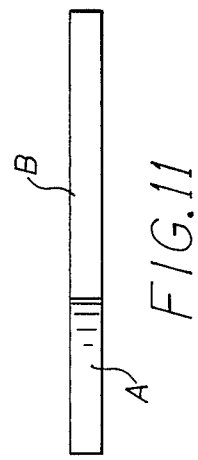
FIG. 11 is an edge elevation of the cassettes shown in FIGS. 5, 9 and 10.
Figure 9:
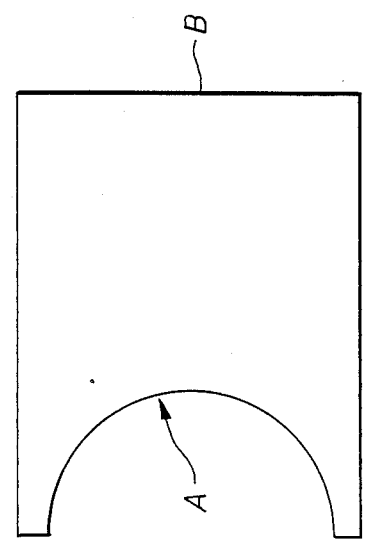
FIG. 9 shows a view of the X-ray cassette from above consisting of a box for holding an X-ray film having an edge wall portion contoured for a different application.

In FIGS. 9 and 10, there are shown X-ray cassettes B consisting of a box for holding an image fixing medium, i.e., X-ray film, having an edge wall portion or portions A contoured for other applications requiring a fit against a particular surface. The thickness of the cassette B and contoured edge wall A are shown in FIG. 11.

In FIG. 12, there is shown an X-ray cassette B consisting of a box for holding an X-ray film having an edge wall portion A contoured as in FIG. 5 or 9 fitting the stomach wall C and positioned to evaluate an umbilical hernia D.

Figure 14:
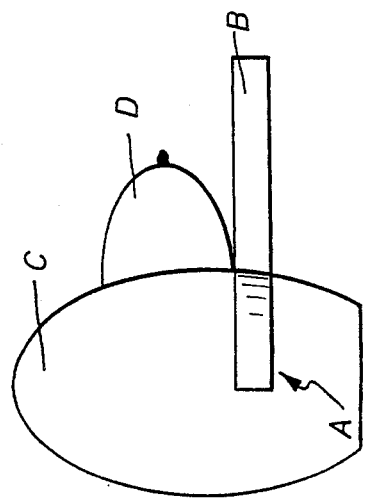
FIG. 14 shows a view of the X-ray cassette from side to evaluate the human breast.
Figure 13:
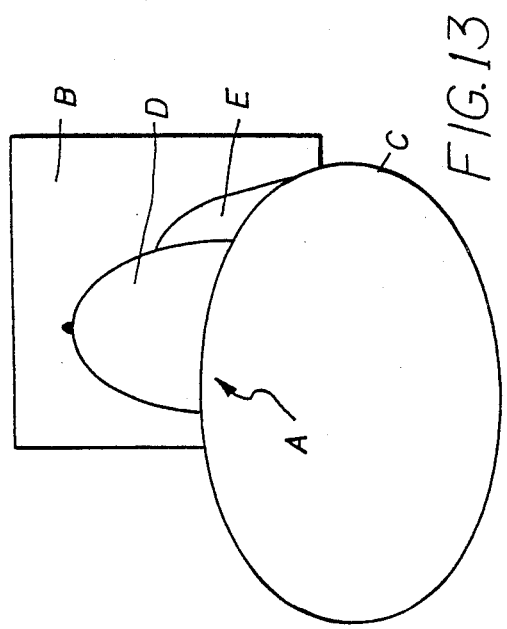
FIG. 13 shows a view of the X-ray cassette from above consisting of a box for holding an X-ray film having an edge wall portion contoured to fit and fitted against a female or male body portion adjacent to the breast.

In FIGS. 13 and 14, an X-ray cassette B consists of a box for holding a contoured X-ray film having an edge wall portion A contoured to fit and fitted against a female or male chest C adjacent to the breast D. This arrangement permits a more thorough examination of the breast D and auxiliary slip E in that deeper breast tissue and auxiliary slip are completely submitted for detection. An X-ray beam presented perpendicularly to the cassette B and the film supported therein allows a more complete examination of these structures. Standard cassettes are geometrical in shape and preclude this detection.

Figure 15:
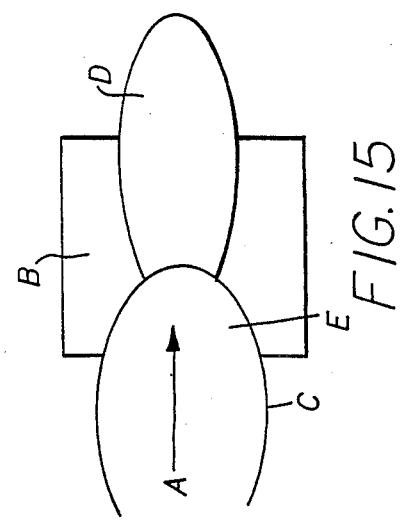
FIG. 15 shows a view of the X-ray cassette from top to evaluate the shoulder and upper arm extending from the chest.

In FIG. 15, cassette B has surface A contoured to fit the chest C and positioned to evaluate the shoulder E and upper arm D.

The various sections of the X-ray energy source/detector axis are specifically and complimentary contoured for use with the cassettes just described. FIG. 7 shows hoe the detectable energy source or X-rays are contoured by shielding material, such as contoured lead sheet, in the collimator, D, and cone device, C, by placing the shielding material within this structures as in FIG. 8, S. FIG. 7 shows how the remaining structures in the axis are contoured in a complimentary manner, as is the energy source. The compression plate, A, is contoured, the cassette, B, is contoured, and the cassette holder/exposure monitor plate, H, is contoured. This allows the energy source to almost match the configuration of the detection device and supporting or additional structures in the axis, FIG. 5 and 6 indicates that all internal parts of a contoured cassette, film, grids, shielding materials, support material, and intensifying screens are similarly and, almost exactly, contoured to the configuration of the contoured cassette outline. Any device used with the contoured imaging system is similarly contoured as, F, FIG. 1, a contoured biopsy plate. The cassettes, as shown and described in FIGS. 5 and 9 - 15, are all useful in combination with a contoured X-ray source and system as described above.

While this invention has been shown fully and completely with special emphasis on certain preferred embodiments, it should be understood that within the scope of the appended claims the invention may be practiced otherwise than as specifically described herein.

I claim:

1. An X-ray imaging system comprising,
   a source means for generating X-rays for examination of the interior of objects and spaced from the object to be examined, and
   an X-ray film cassette positioned on the other side of the object to be examined for detection of X-rays transmitted from said source means through the object to be examined,
   said cassette being a box of a material permitting transmission of X-rays from said source means, said box having an edge wall portion with a concave contour for receiving an image fixing medium having the same concave contour, an X-ray film positioned removably inside said box having a contour fitting the inside of said contoured edge wall, said contoured edge of said box being shaped to fit around the surface of an object adjacent to the portion of the object to be subjected to detectable energy to position the image fixing medium therein more closely in line with the energy being transmitted thereto, and said source means including means to contour an X-ray beam therefrom to pass only through the portion of the object being examined to reach said image fixing medium adjacent to the contoured edge thereof.

2. An imaging system according to claim 1, in which said means to contour an X-ray beam contours said beam in substantially the shape of said contoured X-ray film cassette.

3. An imaging system according to claim 1 in which said means to contour an X-ray beam is a contoured shield obstructing or absorbing a predetermined portion of said beam to contour the same in substantially the shape of said contoured X-ray film cassette.

4. An imaging system according to claim 1 in which said means to contour an X-ray beam is a contoured lead shield obstructing or absorbing a predetermined portion of said beam to contour the same in substantially the shape of said contoured X-ray film cassette.

5. An imaging system according to claim 1 in which said source means is contoured to emit an X-ray beam in substantially the shape of said contoured X-ray film cassette.

6. An imaging system according to claim 1 in which said cassette box is constructed of cardboard or plastic and openable for insertion of a contoured X-ray film.

7. An imaging system according to claim 1 in which said cassette box edge wall portion is contoured to fit against and at least partially around a human body portion so that the cassette may position the edge of a contoured X-ray film in close contact with the body adjacent and around a body part to be X-rayed.

8. An imaging system according to claim 1 in which said cassette box edge wall portion is contoured to fit against and at least partially around a curved surface of a body so that the cassette may position the contoured edge of an X-ray film in close contact with said surface adjacent a portion of said body to be X-rayed.

9. An imaging system according to claim 1 in which said box is constructed for use in radiology.

10. An imaging system according to claim 1 in which said box is constructed for use in mammography.

11. An imaging system according to claim 1 in which said cassette box edge wall portion has a plurality of contours.

* * * * *